US00PP13344P3

(12) United States Plant Patent
Utecht

(10) Patent No.: US PP13,344 P3
(45) Date of Patent: Dec. 10, 2002

(54) GERANIUM PLANT NAMED 'FISBLIZDARK'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/800,496

(22) Filed: Mar. 8, 2001

(65) Prior Publication Data

US 2002/0129428 P1 Sep. 12, 2002

(51) Int. Cl.[7] ..... A01H 5/00
(52) U.S. Cl. ..... Plt./332
(58) Field of Search ..... Plt./332

(56) References Cited

PUBLICATIONS

GTITM UPOVROM Citation for 'Fisblizdark' as per QZ PBR 991464; Oct. 20, 1999.*
GTITM UPOVROM Citation for 'Fisblizdark' as per CA PBR 99–1882; Nov, 30, 1999.*
Fischer Website, New Geranium Varieties for 2000–2001; 2000.*
Windmill–Farms Website, Ivy Geraniums Products; 2000.*
Ball Seed Website, Geranium; 2000.*
Euroamerican Propagators Website; Cultivar Information for 'Dark Red Blizzard' for 2001/2001 catalog; 2001.*
Bulletin des Variétés Végétales, No. 42, Canadian Plant Breeders' Rights Office, Jan. 2002.
Official Gazette of the Community Plant Variety Office, European Community, Dec. 15, 1999.

* cited by examiner

*Primary Examiner*—Kent L. Bell
(74) *Attorney, Agent, or Firm*—Foley & Lardner

(57) ABSTRACT

A new and distinct cultivar of geramium plant named 'Fisblizdark', as described and illustrated, and particularly characterized by the combined features of dark-red, single flowers, large umbels and rich flowering, intense green, slightly zoned foliage, and tall, trailing, though well-branched plant habit.

2 Drawing Sheets

LATIN NAME OF THE GENUS AND SPECIES OF THE PLANT CLAIMED

*Pelargonium peltatum* L'Héritier ex Aiton.

VARIETY DENOMINATION:

'Fisblizdark'.

BACKGROUND OF THE INVENTION

The present invention comprises a new and distinct cultivar of geranium, botanically known as *Pelargonium peltatum*, and hereinafter referred to by the cultivar name 'Fisblizdark'. 'Fisblizdark' is a product of a planned breeding program which had the objective of creating new ivy geranium cultivars with single type flowers, relatively vigorous, but well-branched growth habit, and in various flower colors. 'Fisblizdark' originated from a hybridization made by the inventor Angelika Utecht in a controlled breeding program in Galadar, Gran Canaria, Spain, in 1996.

The female parent was the variety 'Fiscoral', U.S. Plant Pat. No. 12,295, having orange-red, double flowers, fresh-green, slightly zoned foliage, and tall, well-branched plant habit. The male parent of 'Fisblizdark' was a hybrid seedling, no. 823/39 (unpatented), derived from a cross with 'Fisrock', U.S Plant Pat. No. 10,365, and characterized by deep red single-type flowers, medium-green, zoned folige, and medium to tall plant habit.

'Fisblizdark' was selected as one flowering plant within the progeny of the stated cross by Angelika Utecht in a controlled environment in Galdar, Gran Canaria, Spain, in 1997.

The first act of asexual reproduction of 'Fisblizdark' was accomplished when vegetative cuttings were taken from the initial selection in the fall of 1997 in a controlled environment in Galdar, Gran Canaria, Spain, by, or under the supervision of, Angelika Utecht. Horticultural examination of plants grown from these cuttings initiated in the spring of 1998 in Hillscheid, Germany, and continuing thereafter, has demonstrated that the combination of characteristics as herein disclosed for 'Fisblizdark' are firmly fixed and are retained through successive generations of asexual reproduction.

'Fisblizdark' has not been observed under all possible environmental conditions. The phenotype may vary significantly with variations in environment such as temperature, light intensity and day length.

BRIEF DESCRIPTION OF THE INVENTION

The following observations, measurements, and comparisions describe plants grown in Hillscheid, Germany, and in Langley, British Columbia, Canada, under greenhouse conditions which approximate those generally used in commercial practice.

The following traits have been repeatedly observed and are determined to be basic characteristics of 'Fisblizdark', which in combination distinguish this geranium as a new and distinct cultivar:

1. Dark-red colored, round, single-type flowers;
2. Large, flat semi-sperically shaped umbels;

3. Relatively dark-green, smallish, and slightly zoned leaves;

4. Vigorous growth and relatively tall, trailing, through well-branched plant habit; and 5. Early spring flowering response.

Of the many commercil cultivars known to the present inventor, the most similar in comparision to 'Fisblizdark' is 'Fizzard', U.S. Plant Pat. No. 10,992. In comparison to 'Fizzard', 'Fisblizdark' has a distinctly darker red flower color, slightly shorter upper petals and therefore more round shaped flowers, and darker green, smaller, somewhat stronger zoned leaves with entire margins, while 'Fizzard' develops weak crenation near the tips. Furthermore, flowering response of 'Fisblizdark' is early, but not extremely early, as with 'Fizzard'.

BRIEF DESCRIPTION OF THE DRAWING

The accompanying photographic drawings show typical flower and foliage characteristics of 'Fisblizdark' with colors being as true as possible with illustrations of this type.

The photograph on sheet one depicts a typical plant of 'Fisblizdark'.

The photograph on sheet 2 depicts a close up view of typical flowers and leaves of 'Fisblizdark'.

DETAILED BOTANICAL DESCRIPTION

The measurements were taken in Langley, Canada, on Jul. 20, 2000. The plants were growing in 6 inch pots in a greenhouse, and had had 15 weeks of cultivation time from the planting of rooted cuttings on Apr. 3, 2000. The plants had not been pinched.

In the following description color references are made to The Royal Horticultural Society Colour Chart (R.H.S.). The color values were determined indoors from plants developed in a greenhouse in May, 200, in Hillscheid, Germany.

INFLORESCENCE

Lastingness of the bloom: Individual flower lasts about 7 days at 18° C., umbel lasts about 12–14 days.

Fragrance: None.

Umbel:

*Shape.*—Almost semi-spherically, somewhat irregular.

*Average diameter.*—119 mm.

*Average depth.*—50 mm.

*Peduncle length.*—133 mm.

*Peduncle color.*—Medium green, RHS 143 A to 143 B.

*Pedicel length.*—35 mm, with spur.

*Pedicel color.*—Mainly dark-violet, RHS 59A to RHS 61A.

*Number of flowers per umbel.*—About 7–10.

Corolla:

*Average diameter.*—49 mm.

*Average depth.*—Approximately 10 mm.

*Form.*—Single-type.

*Shape.*—Nearly round outline.

*Number of petals.*—5.

*Size.*—Upper petals are about 30 mm long and 15–17 mm wide; lower petals are 23–25 mm long and 17–18 wide.

*Shape.*—Upper petals are spatulate with attenuate base, upper end rounded; lower petals are obovate, with rounded tips and attenuate base; margins are entire or very weakly notched at the tip of the petal.

*Color* (*general tonality from a distance of three meters*). —Dark red.

*Color of upper petals.*—RHS 46 A.

*Markings of upper petals.*—Black stripes (veins) at the base of upper petals, RHS 187 A.

*Color of lower petals.*—RHS 46 A.

*Color of lower surface of petals.*—RHS 46 B to 53 B.

*Color of sepals.*—Lower surface grass-green, RHS 143 A; largest sepal partly brownish, RHS 178 B; upper surface lighter green RHS 143 B.

*Size of sepals.*—Length 10–12 mm; width 4–5 mm for largest, upper sepal; 2–3 mm in width for other sepals.

*Shape of sepals.*—Linear to lanceolate, acute tip; truncate base; surface with weak pubescence; margin entire.

*Number of sepals.*—5.

Bud: (just prior to petals unfolding):

*Shape.*—Narrow elliptic to asymmetric.

*Sepal color* (*lower part*).—Grass-green, RHS 143 A.

*Petal color* (*upper part*).—Deep red, between RHS 46 A and 46 B.

*Length.*—19 mm.

*Width.*—8 mm.

Reproductive organs:

*Androecium.*—7 fertile anthers, with whitish filaments, orange pollen the lower side of the mature (open) anther is black.

*Gynoecium.*—5–6-lobed, purple stigma, RHS 61 B, whitish style; one pistil per flower.

*Fertility/seed set.*—Weak seed set through the summer, more seeds are developed from late summer to autumn.

*Fruit.*—Oblong, about 6 mm, rostrate with rostrum (beak) 38–40 mm long.

*Seed.*—Oblong, 4–5 mm, brown RHS 177 A.

*Amount.*—From late summer on approximately 30% of the flowers of an inflorescence seed set, depending on weather conditions.

Spring flowering response period: In Hillscheid, Germany, in 2000, plants had on average 2.1 flowers opened 12 weeks after planting of rooted cuttings (pinched plants).

Outdoor flower production: Rich and continuously flowering, the flower count in Hillscheid, Germany, indicated about 4–5 inflorescences per plant in mid May.

*Durability.*—Relatively good shatter resistance for a single-flowered variety, good rain resistance, petal color may slightly fade when maturing.

*Pest/disease resistance/susceptibility.*—Good tolerance to botrytis, due to the smooth, glossy foliage surface.

PLANT

Foliage:

*Shape.*—Ivy-shaped with distinct lobes with rounded tips, nearly closed cordate base.

*Texture.*—Glossy surface.

*Margin.*—Entire, apart from the lobes.

*Size of leaf.*—75 mm wide, 45 mm long.

*Color of upper surface.*—Medium to dark green, between RHS 137 A and 137 B.

*Color of lower surface.*—Closest to RHS 137 C.

*Petioles.*—50–70 mm long, 2–3 mm diameter, color about RHS 143 C.

*Color of zonation.*—Brown, near RHS 166 A, forming a narrow ring.

General appeaarance and form:

*Internode length.*—45–55 mm.

*Branchng pattern.*—6.6 branches.

*Length of branches.*—65 cm (15 week old plants in Langley, Canada) 100–110 cm in mid September in Hillscheid, Germany 31 weeks old well-branched plant habit (branches measured from the soil level to the tips of the branches without inflorescences).

I claim:

1. A new and distinct cultivar of geranium plant named 'Fisblizdark', as described and illustrated.

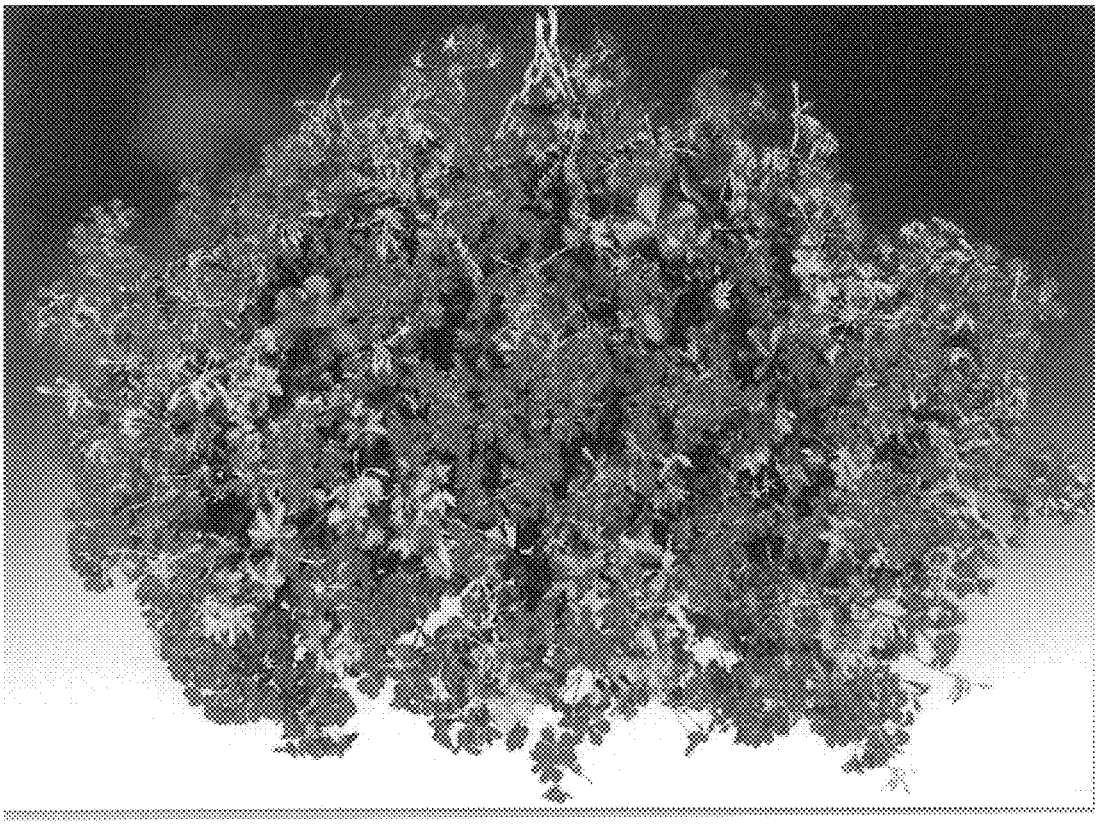

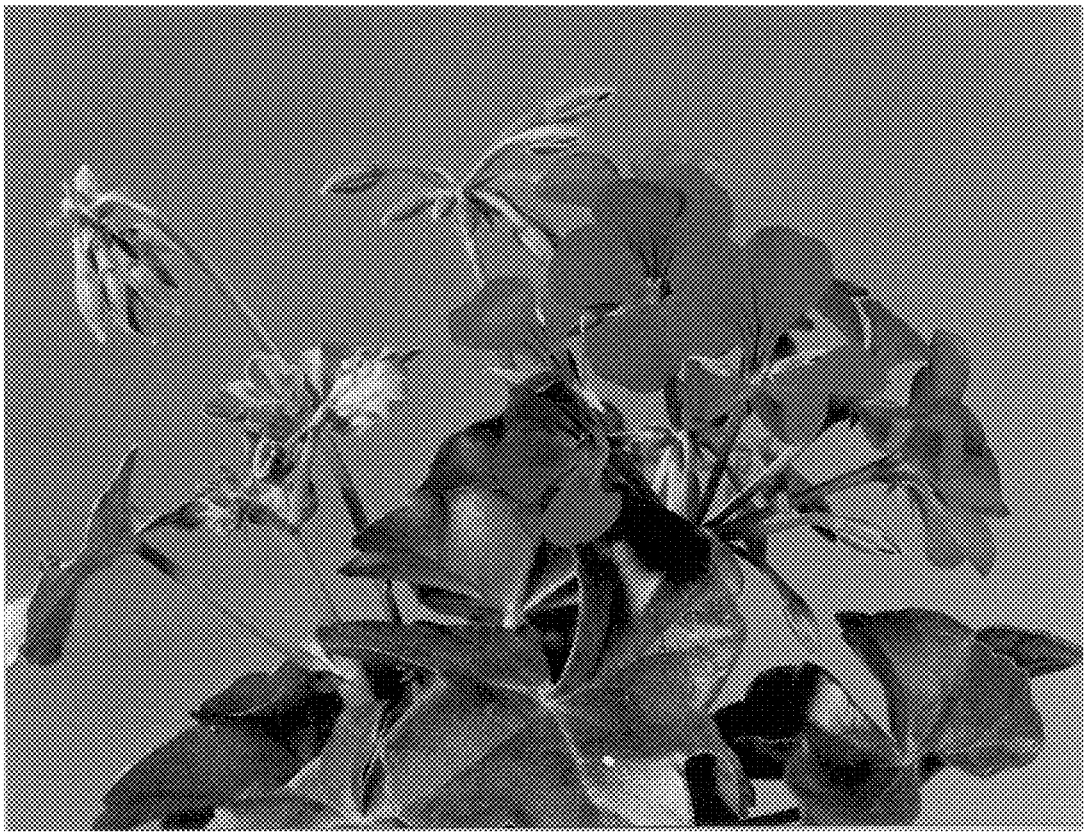

* * * * *